US008177826B2

(12) United States Patent
Grahn et al.

(10) Patent No.: US 8,177,826 B2
(45) Date of Patent: *May 15, 2012

(54) METHODS AND DEVICES FOR EXTRACTING THERMAL ENERGY FROM THE BODY CORE OF A MAMMAL

(75) Inventors: Dennis A. Grahn, Palo Alto, CA (US); H. Craig Heller, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1987 days.

This patent is subject to a terminal disclaimer.

(21) Appl. No.: 11/246,915

(22) Filed: Oct. 6, 2005

(65) Prior Publication Data

US 2006/0111766 A1    May 25, 2006

(51) Int. Cl.
*A61F 7/00* (2006.01)
(52) U.S. Cl. .......................................... 607/104; 607/96
(58) Field of Classification Search .................. 607/104, 607/108, 111, 112
See application file for complete search history.

(56) References Cited

U.S. PATENT DOCUMENTS

| 4,376,437 A | 3/1983 | Sundheim et al. |
| 5,358,467 A | 10/1994 | Milstein et al. |
| 5,683,438 A | 11/1997 | Grahn |
| 5,688,225 A | 11/1997 | Walker |
| 6,149,674 A | 11/2000 | Borders |
| 6,656,208 B2 * | 12/2003 | Grahn et al. ................... 607/104 |
| 6,974,442 B2 * | 12/2005 | Grahn et al. ................... 604/104 |

FOREIGN PATENT DOCUMENTS

| EP | 0325 771 | 8/1989 |
| WO | 98/40039 | 10/1998 |
| WO | WO 99/23980 | 5/1999 |

OTHER PUBLICATIONS

Bergersen et al. "Perfusion of the Human Finger During Cold-Induced Vasodilation," American Physiological Society, (1999) R731-R737.
Bergersen et al. "Local Constriction of Arteriovenous Anastomosis in the Cooled Finger," American Physiological Society (1997) R880-R886.

(Continued)

*Primary Examiner* — Roy Gibson
*Assistant Examiner* — Jared W Pike
(74) *Attorney, Agent, or Firm* — Bozicevic, Field & Francis LLP; Bret E. Field

(57) ABSTRACT

Methods and devices for extracting thermal energy from the core body of a mammal are provided. In practicing the subject methods, a portion of the mammal, e.g. a limb or portion thereof, is placed in a sealed enclosure to produce an enclosed portion of the mammal. A surface of the enclosed portion of the mammal is then contacted with a low temperature medium under negative pressure conditions for a period of time sufficient to provide for the desired core body thermal energy extraction. The subject methods and devices find use in a variety of applications, e.g. providing relief from temperature sensitive disorders, such as multiple sclerosis, and the treatment of hyperthermia, among other treatments. The subject methods and devices are particularly suited for use in enhancing the physical ability of a mammal.

11 Claims, 11 Drawing Sheets

OTHER PUBLICATIONS

Bergersen et al. "Effect of Local Warming in Hand and Finger Artery Blood Velocities," American Physiological Society, (1995) R325-R330.

Wachter, "New Device Could Reduce Rewarming Time from Anesthesia Hypothermia," Anesthesiology News (1997), p. 1.

"Hypothermia Rewarmer Launched in Postoperative Market Dec. 4, 1998," MDI Business Advisor (1998).

Thermo-STAT Operations Manual, Aquarius Medical Corporation, (1998).

Booth et al. "Improved Running Performance in Hot Humid Conditions Following Whole Body Precooling," Med Sci Sports Exerc. (1997), 29(7):943-9.

Brown et al., "The Effect of Head Cooling on Deep Body Temperature and Thermal Comfort in Man," Aviat. Space Environ Med. (1982), 53:583-586.

Bruck et al, "Body Temperature Related Factors Diminishing the Drive to Exercise," Can J Physiol Pharmacol. (1987), 65(6):1274-80.

Capello et al., "Lowering Body Temperature with a Cooling Suit as Symptomatic Treatment for Thermosensitive Multiple Sclerosis Patients," Ital. J. Neurol Sci. (1995), 16:533-539.

Gonzalez-Alonso et al., "Influence of Body Temperature on the Development of Fatigue During Prolonged Exercise in the Heat," J Appl Physiol. (1999), 86(3):1032-9.

Gordon et al. "Effect of a Practical Neck Cooling Device on Core Temperature During Exercise," Med. Sci. Sports Exerc. (1990), 22:245-249.

Grahn et al., "Recovery from Mild Hypothermia Can Be Accelerated by Mechanically Distending Blood Vessels in the Hand," J. Appl. Physiol. (1998), 85(5):1643-8.

Greenhaff et al., "Predictors of Sweat Loss in Man During Prolonged Exercise," Eur. J. Appl. Physiol. (1989), 58(4):348-52.

Hessemer et al, "Effect of Slightly Lowered Body Temperatures on Endurance Performance in Humans," J. Appl. Physiol. (1984), 57(6):1731-7.

Katsuura et al., "Effects of Cooling Portions of the Head on Human Thermoregulatory Response," Appl. Human Sci. (1996), 15:67-74.

Ku et al., "Physiologic and Thermal Responses of Male and Female Patients with Multiple Sclerosis to Head and Neck Cooling," Am. J. Phys. Med. Rehabil. (1999), 78:447-456.

Ku et al., "Hemodynamic and Thermal Responses to Head and Neck Cooling in Men and Women," Am. J. Phys. Med. Rehabil. (1996), 75:443-450.

Lee et al., "Exercise Duration and Thermoregulatory Responses After Whole Body Precooling," J. Appl. Physiol. (1995), 79(6):1971-6.

Leweke et al. "Temperature Effects on Ventilatory Rate, Heart Rate, and Preferred Pedal Rate During Cycle Ergometry," J. Appl. Physiol. (1995), 79(3):781-5.

Marsh et al. Effect of Precooling on High Intensity Cycling Performance, Br. J. Sports Med. (1999), 33(6):393-7.

Olschewski et al., "Thermoregulatory, Cardiovascular, and Muscular Factors Related to Exercise After Precooling," J. Appl. Physiol. (1988), 64(2):803-11.

Schmidt et al."Effect of a Precooling Maneuver on Body Temperature and Exercise Performance," J. Appl. Physiol. (1981), 50(4):772-8.

Soreide et al., "A Non-Invasive Means to EffectivelyRestore Normothermia in Cold Stressed Individuals: A Preliminary Report," J Emerg. Med. (1999), 17(4):725-30.

Watanuki, S., "Effects of Head Cooling on Cardiovascular and Body Temperature Responses During Submaximal Exercise," Ann. Physiol. Anthropol. (1993), 12:327-333.

* cited by examiner

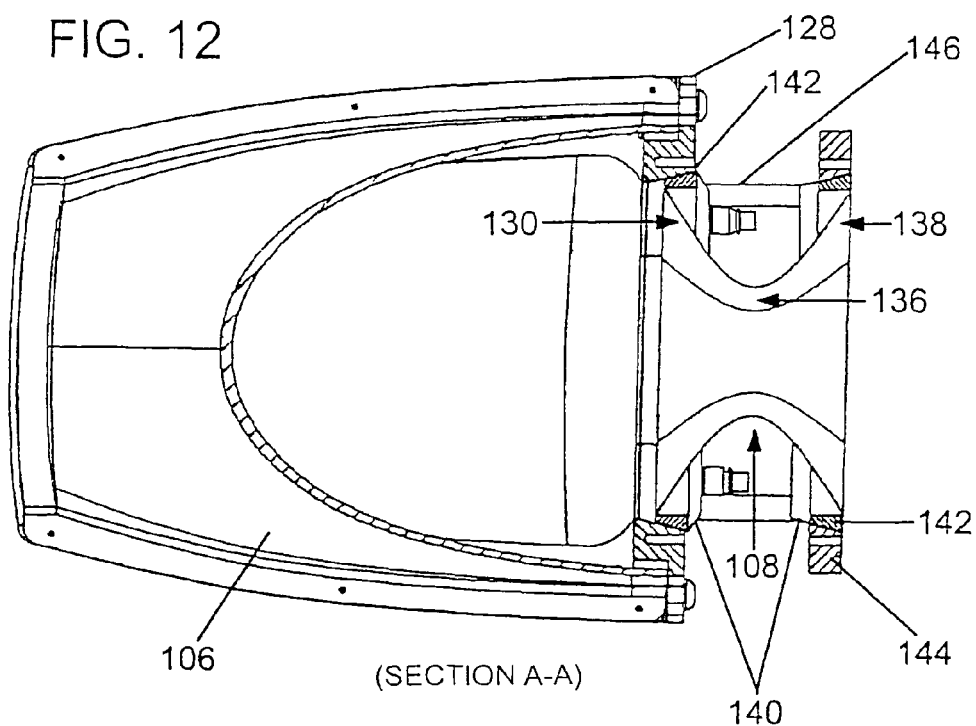
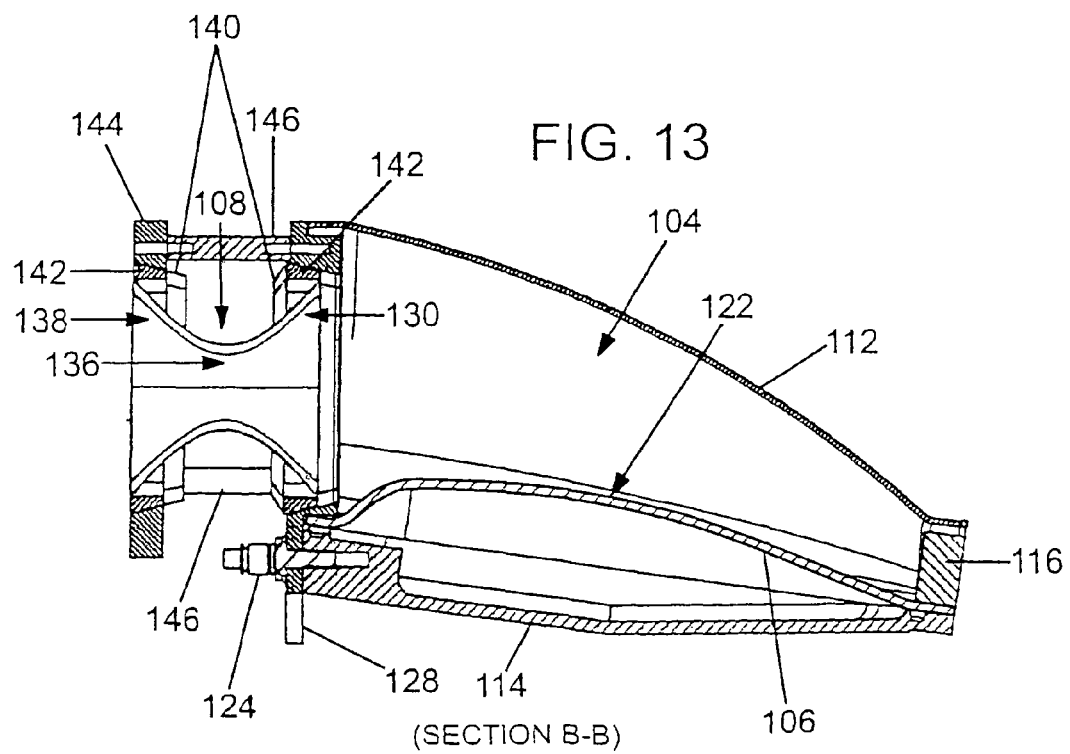

METHODS AND DEVICES FOR EXTRACTING THERMAL ENERGY FROM THE BODY CORE OF A MAMMAL

FEDERALLY SPONSORED RESEARCH AND DEVELOPMENT

This invention was made with Government support under contract NBCH1030020 awarded by The Department of the Interior, contract M67854-00-C-2144a, awarded by the Marine Corps Systems Command, and contracts DAMD17-03-2-0029, W911NF-05-1-0548, W911NF-07-1-0098 awarded by The Department of the Army. The Government has certain rights in this invention.

CROSS REFERENCE TO RELATED APPLICATIONS

Pursuant to 35 U.S.C. §119 (e), this application claims priority to the filing date of the U.S. Provisional Patent Application Ser. No. 60/199,016 filed Apr. 20, 2000 and U.S. Provisional Patent Application Ser. No. 60/199,015 filed Apr. 20, 2000; the disclosures of which are herein incorporated by reference.

INTRODUCTION

1. Field of the Invention

The field of this invention is core body energy regulation.

2. Background of the Invention

Instances exist where it is desired to extract thermal energy or heat from the body core of a mammal. For example, there are many instances in which it is desired to lower the internal body temperature of a subject. Instances where it is desired to extract heat from the body core of a subject include the treatment of hyperthermia, including self-induced hyperthermia resulting from work or exercise, and the treatment of temperature sensitive disorders, such as multiple sclerosis. For example, personal cooling systems are employed to alleviate symptoms of multiple sclerosis. In such methods, a patient wears a personal cooling system, e.g. a cooling helmet or garment, for a certain period of time during the day to alleviate symptoms.

While a number of different methodologies and devices have been developed for use in reducing the core body temperature of a subject, there continues to be a need for the development of new devices and protocols. Of particular interest would be the development of a device and protocol that provided for efficient heat extraction from the body core in a non-invasive manner that would be readily used by subjects, i.e. enjoy high patient compliance.

Relevant Literature

U.S. Pat. No. 5,683,438. See also WO 98/40039. Also of interest are: Soreide et al., "A non-invasive means to effectively restore normothermia in cold stressed individuals: a preliminary report," J Emerg. Med. (1999 July-August)17(4): 725-30 and Grahn et al., "Recovery from mild hypothermia can be accelerated by mechanically distending blood vessels in the hand," J. Appl Physiol. (1998) 85(5):1643-8. See also: Ku et al., Am. J. Phys. Med Rehabil. (September-October 1999) 78:447-456; Ku et al., Am. J. Phys. Med. Rehabil. (November-December 1996) 75:443-450; Capello et al., Ital. J. Neurol Sci. (1995) 16: 533-539; Brown & Williams, Aviat. Space Environ Med. (1982) 53:583-586; Gordon et al., Med. Sci. Sports Exerc. (1990) 22:245-249; Watanuki, Ann. Physiol. Anthropol. (1993) 12:327-333; and Katsuura et al., Appl. Human Sci. (1996) 15:67-74. See also: Bruck K, Olschewski H. Body temperature related factors diminishing the drive to exercise. Can J Physiol Pharmacol. 1987 June; 65(6):1274-80; Schmidt V, Bruck K. Effect of a precooling maneuver on body temperature and exercise performance. J Appl Physiol. 1981 April; 50(4):772-8; Hessemer V, Langusch D, Bruck L K, Bodeker R H, Breidenbach T. Effect of slightly lowered body temperatures on endurance performance in humans. J Appl Physiol. 1984 December; 57(6): 1731-7; Olschewski H, Bruck K. Thermoregulatory, cardiovascular, and muscular factors related to exercise after precooling. J Appl Physiol. 1988 February; 64(2):803-11; Booth J, Marino F, Ward J J. Improved running performance in hot humid conditions following whole body precooling. Med Sci Sports Exerc. 1997 July; 29(7):943-9; Greenhaff P L, Clough P J. Predictors of sweat loss in man during prolonged exercise. Eur J Appl Physiol. 1989; 58(4):348-52; Leweke F, Bruck K, Olschewski H. Temperature effects on ventilatory rate, heart rate, and preferred pedal rate during cycle ergometry. J Appl Physiol. 1995 September; 79(3):781-5; Lee D T, Haymes E M. Exercise duration and thermoregulatory responses after whole body precooling. J Appl Physiol. 1995 December; 79(6):1971-6; Marsh D, Sleivert G. Effect of precooling on high intensity cycling performance. Br J Sports Med. 1999 December; 33(6):393-7; and Gonzalez-Alonso J, Teller C, Andersen S L, Jensen F B, Hyldig T, Nielsen B. Influence of body temperature on the development of fatigue during prolonged exercise in the heat. J Appl Physiol. 1999 March; 86(3):1032-9.

SUMMARY OF THE INVENTION

Methods and devices for extracting thermal energy from the body core of a mammal are provided. In practicing the subject methods, a portion of the mammal, e.g. a limb or portion thereof, is placed in a sealed enclosure to produce an enclosed portion of the mammal. A surface of the enclosed portion of the mammal is then contacted with a low temperature medium under negative pressure conditions for a period of time sufficient to extract the desired amount of heat from the body core of the mammal. The subject methods and devices find use in a variety of applications, e.g. providing relief from temperature sensitive disorders, such as multiple sclerosis, and the treatment of hyperthermia.

The subject methods are particularly suited for use in enhancing the physical ability of a mammal. In these embodiments, thermal energy is extracted from the core body of the mammal during the physical procedure for a period of time sufficient to enhance the ability of the mammal to perform the physical procedure. To extract thermal energy from the core body of the mammal in the subject methods, a portion of the mammal, e.g., a limb or portion thereof, is placed in a sealed enclosure to produce an enclosed portion of the mammal. A surface of the enclosed portion of the mammal is then contacted with a low temperature medium under negative pressure conditions for a period of time sufficient to provide for the requisite core body thermal energy extraction. The subject methods and devices find use in the enhancement of the ability of a mammal to perform a variety of different physical procedures, including athletic procedures.

BRIEF DESCRIPTION OF THE FIGURES

FIGS. 8 to 13 provide various views of a device that can be employed to practice to the subject methods.

DESCRIPTION OF THE SPECIFIC EMBODIMENTS

Figure 1:
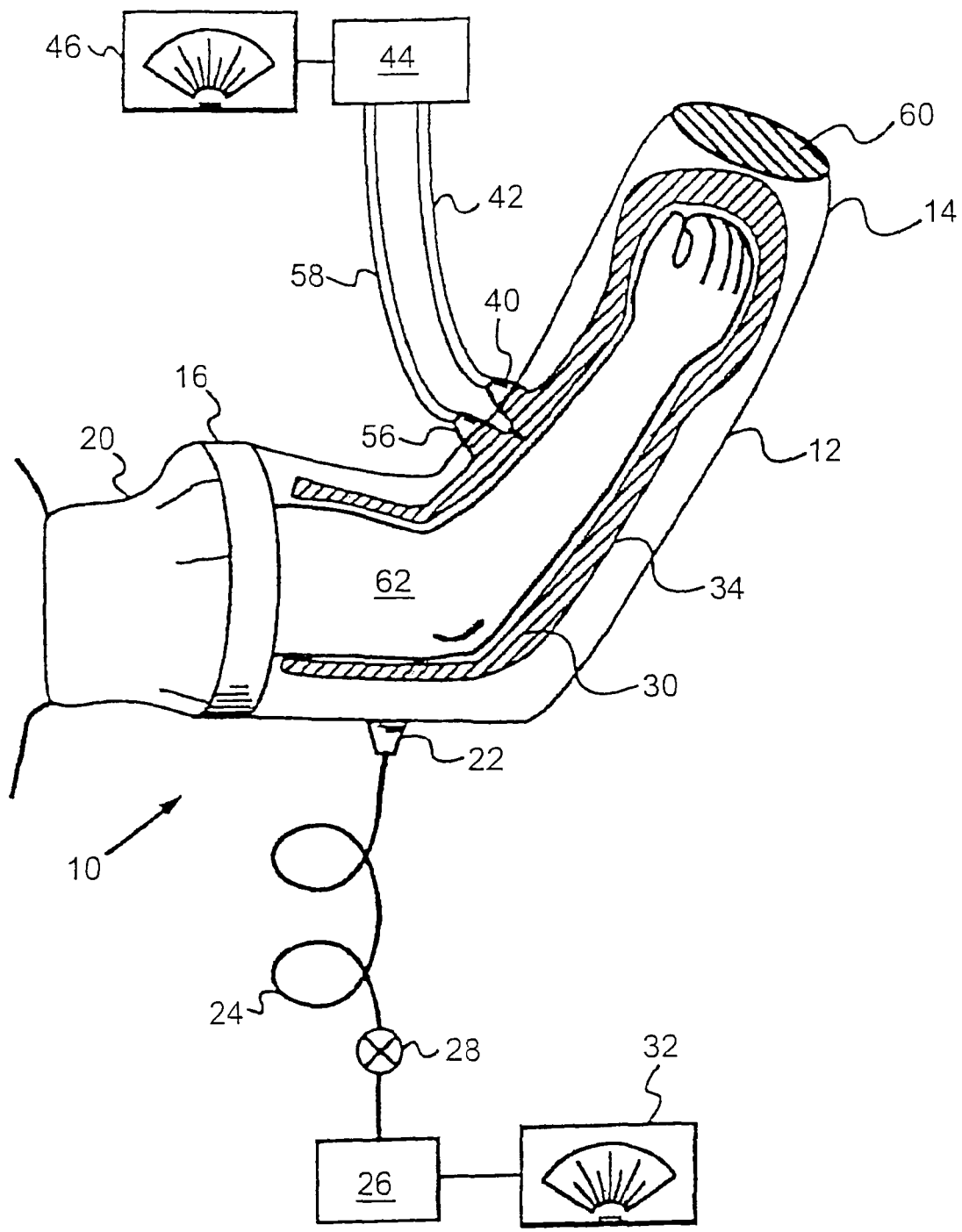
FIG. 1 provides a representation of a device according to the subject invention.

Methods and devices for extracting thermal energy from the body core of a mammal are provided. In practicing the subject methods, a portion of the mammal, e.g. a limb or portion thereof, is placed in a sealed enclosure to produce an enclosed portion of the mammal. A surface of the enclosed portion of the mammal is then contacted with a low temperature medium under negative pressure conditions for a period of time sufficient to extract the desired amount of heat from the body core of the mammal. The subject methods and devices find use in a variety of applications, e.g. providing relief from temperature sensitive disorders, such as multiple sclerosis, and the treatment of hyperthermia.

The subject methods are particularly suited for use in enhancing the physical ability of a mammal. In these embodiments, thermal energy is extracted from the core body of the mammal during the physical procedure for a period of time sufficient to enhance the ability of the mammal to perform the physical procedure. To extract thermal energy from the core body of the mammal in the subject methods, a portion of the mammal, e.g., a limb or portion thereof, is placed in a sealed enclosure to produce an enclosed portion of the mammal. A surface of the enclosed portion of the mammal is then contacted with a low temperature medium under negative pressure conditions for a period of time sufficient to provide for the requisite core body thermal energy extraction. The subject methods and devices find use in the enhancement of the ability of a mammal to perform a variety of different physical procedures, including athletic procedures.

In further describing the subject invention, the subject methods and representative applications will be discussed in greater detail, followed by a review of representative devices for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Methods

As summarized above, the subject invention provides methods for extracting heat or thermal energy from the body core of a mammal. By core body is meant the internal body region or portion of the mammal, as opposed to the surface of the mammal.

In certain embodiments, the subject invention provides methods for enhancing the ability of mammal to perform a physical procedure. By enhancing is meant improving or bettering the ability of the mammal to perform a particular physical procedure, task or operation. In many embodiments, this enhancement is distinct from a reduction in recovery time of the mammal during a physical task or procedure, such that the subject methods result in not a reduction in recovery time (although this may be a manifestation) but also result in some additional improvement or enhancement. The nature of the enhancement may vary depending on the specific nature of the physical task. For example, where the physical procedure or task is an athletic procedure, e.g. participation in a game, a training or exercise routine, a long distance run or swim, etc., the enhancement is generally in the form of an improvement in the athletic ability of the mammal to perform the athletic procedure, e.g. by increasing the length of time a participant can play in a game (at peak performance), increasing workout capacity, improving the training program (e.g. by increasing the time an individual can train, increasing the number of weight repetitions that can be done, improving a training regimen, etc.) so that an individual can perform a particular task, e.g. race, better, etc. Likewise, where the physical procedure or task is a work or employment related procedure or task, the enhancement may be in the form of increased output from the work or related procedure over a given period of time. Further examples of different types of enhancements that may be accomplished with the subject methods are provided below in connection with the representative physical procedures in which the subject methods may be employed. In general, the amount of enhancement in ability observed in practicing the subject methods, as compared to a control, is at least about 1.2 fold, usually at least about 1.5 fold and more usually at least about 2.0 fold, where the amount of enhancement may be as high as 6.0 fold or higher.

In practicing the subject methods, thermal energy is extracted from the body core of the mammal at least once during the physical activity to result in the desired ability enhancement. By body core is meant the internal region of the mammal, as opposed to the surface of the mammal. The magnitude of core body thermal energy extraction accomplished during practice of the methods may vary, and is sufficient to provide for the desired outcome, e.g. reduction in core body temperature, ability enhancement, relief from hyperthermia, MS symptoms, etc, and the like. In many embodiments, the magnitude of heat extraction is generally at least about 0.5 Kcal/min, usually at least about 1.0 Kcal/min and more usually at least about 1.5 Kcal/min, where the magnitude may be as great as 50 Kcal/min or greater, but generally does not exceed about 30 Kcal/min and usually does not exceed about 20 Kcal/min. The period of time that the heat is extracted from the core body may vary, but typically ranges from about 1 min to 24 hrs, usually from about 2 min to 20 min and more usually from about 2 min to 5 min.

In certain embodiments, the core body temperature of the subject is reduced. The magnitude of core body temperature reduction is sufficient to provide for the ability enhancement, and is generally at least about 0.5, usually at least about 1.0 and more usually at least about 1.5° C., where the magnitude may be as great as 4° C. or greater, but generally does not exceed about 4.0° C. and usually does not exceed about 2.0° C. The period of time that the core body temperature is reduced may vary, but typically ranges from about 1 min to continuous for duration of activity, usually from about 2 to 20 min and more usually from about 2 to 5 min. In other embodiments, the subject methods will prevent or minimize rises in the core body temperature. Nonetheless, in these embodiments the subject methods do extract heat or thermal energy from the core body of the subject, but the amount of energy being produced by or introduced into the core body of the subject from other sources is substantially the same as or exceeds the amount of energy being extracted from the core body by the subject methods.

Where the specific embodiment is a method of enhancing physical ability, the heat or thermal energy is extracted from the core body at least once during the physical procedure, where the procedure is measure from a point prior to the beginning of the procedure to the end of the procedure, e.g., to the end of a training set, to the end of a game, to the end of a given work day, etc. In certain embodiments, core body heat is extracted a plurality of times. Where core body heat is extracted a plurality of times, the number of different times that heat is extracted typically ranges from about 2 to 20, usually from about 2 to 15 and more usually from about 5 to 10. In certain embodiments, core body thermal energy is extracted a single time. The term procedure is used broadly to include anything from a single physical movement to a plurality of physical movements that are practiced in a given period of time, e.g. participation in a game, performing a particular training regimen, activity encountered during an entire workday etc.

In extracting core body thermal energy from the mammal, a surface of the mammal is contacted with a low temperature medium under negative pressure conditions for a period of time sufficient to achieve the desired reduction in core body temperature. The surface that is contacted with the low temperature medium is generally a heat exchange surface that acts as a heat exchange means between the core body and the environment of the mammal. Heat exchange surfaces of interest with the subject methods include those found in various regions of the mammal, e.g. the arms, legs, palms, soles, head, face, ears, and the like.

By negative pressure conditions is meant a pressure lower than ambient pressure under the particular conditions in which the method is performed, e.g. 1 ATM at sea level. The magnitude of the decrease in pressure from the ambient pressure under the negative pressure conditions is generally at least about 20 mmHg, usually at least about 30 mmHg and more usually at least about 35 mmHg, where the magnitude of the decrease may be as great as 85 mmHg or greater, but typically does not exceed about 60 mmHg and usually does not exceed about 50 mmHg. When the method is performed at or about sea level, the pressure under the negative pressure conditions generally ranges from about 740 to 675, usually from about 730 to 700 and more usually from about 725 to 710 mmHg.

As mentioned above, the surface of the mammal is contacted with a low temperature medium under the negative pressure conditions. By low temperature medium is meant a medium that has a temperature that is sufficient to provide the requisite core body thermal energy or heat extraction or removal. The nature of the medium may vary, the medium being a temperature controlled solid material, e.g. cooling blanket, a liquid, or gas, depending on the particular device employed to practice the subject methods. The temperature of the low temperature medium may vary, but generally is not so low as to cause local vasoconstriction at the surface of the mammal, e.g. the heat exchange surface. The low temperature medium generally has a temperature ranging from about 0 to 35, usually from about 10 to 30 and more usually from about 15 to 25° C. In many embodiments, a feature of the subject methods is that the temperature of the low temperature medium is specifically selected to be one that provides for thermal energy extraction from the core body and not local vasoconstriction.

Contact is maintained for a period of time sufficient for the desired amount of core body thermal energy extraction to occur. As such, contact is generally maintained for at least about 1 min, usually at least about 2 min and more usually at least about 3 min, where contact may be maintained for up to 10 hr or longer, but is generally not maintained for longer than 1 hour and usually is not maintained for longer than 5 min.

In practicing the subject methods, the negative pressure conditions during contact may be static/constant or variable. Thus, in certain embodiments, the negative pressure is maintained at a constant value during contact of the surface with the low temperature medium. In yet other embodiments, the negative pressure value is varied during contact, e.g. oscillated. Where the negative pressure is varied or oscillated, the magnitude of the pressure change during a given period may be varied may range from about −85 to 40 mmHg, usually from about −40 to 0 mmHg, with the periodicity of the oscillation ranging from about 0.25 sec to 10 min, usually from about 1 sec to 10 sec.

In practicing the subject methods, the negative pressure conditions may be provided using any convenient protocol. In many embodiments, the negative pressure conditions are provided by enclosing a portion of the mammal that includes the target surface that is to be contacted with the low temperature medium in a sealed enclosure, where the pressure is then reduced in the sealed enclosure thereby providing the requisite negative pressure conditions. The portion that is enclosed in the sealed enclosure is a portion of the mammal that includes the target heat exchange surface, and therefore is an appendage in many embodiments of the subject invention. As such, the portion that is sealed is an arm or leg, or at least a portion thereof, e.g. hand or foot, in many embodiments of the subject invention. The nature of the enclosure will vary depending on the nature of the appendage to be enclosed, where representative enclosures include gloves, shoes/boots, or sleeves, where the latter is described in greater detail supra in connection with the description of the representative devices that can be used to practice the subject invention.

In certain embodiments, the subject methods may further include a feedback means that at least partially controls when the heat exchange surface of the mammal is contacted with the low temperature medium to extract thermal energy from the core body of the mammal. The feedback means may be any convenient means, where a suitable means is a thermosensor, e.g. placed over a heat exchange surface not being contacted with the low temperature medium. In such embodiments, the method generally further includes a data processing step for processing the feedback data and activating the contact with the low temperature medium in response thereto, e.g. a computing means that controls the contact of the heat exchange surface with the low temperature medium.

The subject methods are suitable or use with a variety of mammals. Mammals of interest include, but are not limited to: race animals, e.g. horses, dogs, etc., work animals, e.g. horses, oxen etc., and humans. In most embodiments, the mammals on which the subject methods are practiced are humans.

Utility

As demonstrated above, the subject methods provide a means for extracting thermal energy or heat from the core body of a mammal. As such, the subject methods are suitable for use in a variety of different applications, where representative applications include the treatment of normal and abnormal physiological conditions, e.g. disease, where core body heat extraction is desirable. Representative applications in which the subject methods find use include the treatment of exercise or work induced hyperthermia, treatment of stroke, treatment of cystic fibrosis symptoms, treatment of multiple sclerosis symptoms, and the like. By treatment is meant at least an alleviation in one or more of the symptoms associated with the condition being treated, e.g. a reduction in discomfort, amelioration or elimination of symptoms, etc.

In many embodiments, the subject methods are employed for enhancing the ability of a mammal to perform a physical procedure or task. As such, the subject methods are suitable for use in a variety of different applications where a variety of different types of physical procedures are performed. For illustration purposes only, the following representative applications are provided. However, it should be noted that the subject methods are suitable for use in the enhancement of the physical ability of a mammal to perform a plethora of other physical procedures not described below.

One type of physical ability that may be enhanced by practicing the subject methods is athletic ability. In other words, the methods may be used to improve the ability of a mammal to perform an athletic procedure. The nature of the improvement or enhancement may vary greatly depending on the nature of the athletic procedure being practiced by the mammal. Representative enhancements include, but are not limited to: increases in strength, e.g. as measured by ability to lift a particular weight, etc.; increases in stamina, e.g. as measured in terms of ability to perform a task or play a sport without resting, etc.; increases in the ability of the mammal to perform repetitions of a physical task, e.g. weight lifts, pull ups, etc; and the like. As mentioned above, the magnitude of the enhancement is generally at least about 1.2 fold, usually at least about 1.5 fold and more usually at least about 2.0 fold, where the magnitude of the enhancement may be as high as 6.0 fold or higher.

Another type of physical ability that may be enhanced by practicing the subject methods is physical work ability. In other words, the subject methods may be used to improve the ability of mammal to perform a particular work related physical procedure. Examples of work related physical procedures include, but are not limited to: physical building and maintenance of equipment, particularly in hot environments; agricultural labor, e.g. crop harvesting; moving office and home furnishings; building and construction, e.g. of homes and offices; civic structure building and maintenance, etc. Enhancement may take many forms including, but not limited to: increasing the number of repetitive movements that may be performed; increasing the length of time a particular job may be performed without resting; reducing errors in a particular job; etc. Again, the magnitude of the enhancement is generally at least about 1.2 fold, usually at least about 1.5 fold and more usually at least about 2.0 fold, where the magnitude of the enhancement may be as high as 6.0 fold or higher.

In many embodiments, the subject methods result in more than a reduction in recovery time to provide some other enhancement or improvement, as exemplified above, e.g., enhanced physical ability, increase workout capacity, etc.

As mentioned above, the above athletic and work related physical procedures are merely representative of the procedures that may be enhanced using the subject methods.

Devices

The above described methods may be practiced using any convenient device. In general, any device that is capable of achieving negative pressure and low temperature medium contact with the target heat exchange surface for the requisite period of time may be employed. In general, devices employed in the subject methods include a means for providing the negative pressure environment at the target heat exchange surface and means for contacting the heat exchange surface with the low temperature medium. In many embodiments, the subject devices include a means for sealing an appendage of the mammal in an enclosed environment in which negative pressure conditions can be produced. Representative enclosing means include sleeves, boots/shoes, gloves, etc. Representative means for contacting the surface with a cooling medium include: cooling blankets, cold water immersion means, cooling gas means, etc.

A representative device for use in practicing the subject methods is provided in FIG. 1. As shown in FIG. 1, core body cooling apparatus 10 includes an enclosing element 12 in the form of a hollow, tubular, elongated sleeve. Sleeve 12 is dimensioned to fit around a body portion 62, preferably an appendage, e.g. arm. In the embodiment illustrated in FIG. 1 appendage 62 is an arm.

Sleeve 12 can be made of virtually any non-hazardous material which retains the requisite shape while the interior of sleeve 12 is maintained at negative pressures. In particular, sleeve 12 has to support negative pressures down to at least −85 mmHg. In a preferred embodiment, sleeve 12 is made of pliant and elastic materials which can include supporting or reinforcing members. This type of construction easily accommodates movements of arm 62 and thus provides the mammal with more comfort and freedom during practice of the subject methods. In the present embodiment sleeve 12 is a neoprene-impregnated polyester sheath supported on a spring steel wire helix.

Sleeve 12, as shown in FIG. 1, has a distal end or rim 14 and a proximal end or rim 16. Distal rim 14 is capped by a sealing element 60 capable of creating an airtight seal. In this embodiment element 60 is a plastic plate. However, a cap or other sealing element can be used with equal success. In certain embodiments, sleeve 12 may be closed off at distal end 14.

A flexible flange 20 is attached to proximal rim 16. Flange 20 is preferably made of a synthetic material impermeable to air. The tubular form of flange 20 ensures that it fits snugly around arm 62 and conforms to the arm's shape. In the present embodiment 20 is made of Neoprene (R).

Elongated sleeve 12 is provided with a pressure inlet 22. A pressure conduit 24, e.g., a flexible tube, is connected to inlet 22. The other end of conduit 24 is connected to a vacuum pump 26. Vacuum pump 26 is a standard pump capable of generating negative pressures down to −85 mmHg and beyond inside sleeve 12. The delivery of this negative pressure through conduit 24 can be regulated by any conventional mechanisms. In the embodiment shown, an adjustable valve 28 guarantees maintenance of the desired pressure inside sleeve 12. Conveniently, a readout gauge 32 is also provided for visual pressure indication.

A cooling element 34 is lodged inside elongated sleeve 12. In the preferred embodiment, cooling element or medium 34 is a cooling blanket filled with a cooling fluid 30. Because of its high heat capacity and general safety, water is particularly well-suited for cooling fluid 30. Cooling blanket 34 extends along the length of sleeve 12 and wraps around arm 62. In certain embodiments, it is desirable that the area of contact between arm 62 and blanket 34 be as large as possible.

Blanket 34 is connected to a fluid inlet 40 and a fluid outlet 56. A supply conduit 42 and a return conduit 58, both preferably made of a flexible tubing, are attached at inlet 40 and outlet 56 respectively. At their other ends conduits 42 and 58 are connected to a cooling and circulating system 44. Preferably, system 44 is a fluid cooler and a circulating pump (not shown). Suitable fluid coolers (e.g. refrigeration means) and pumps are commercially available and commonly known. In addition, system 44 has a control indicator 46 for indicating the temperature of fluid 30 and its rate of flow.

Core body cooling apparatus 10 is simple to use. First, the mammals arm 62 is placed inside sleeve 12 such that cooling blanket 34 envelops arm 62 and remains in contact with it. In this position, flange 20 wraps around the upper portion of arm 62. To ensure that flange 20 conforms closely to the contour of the upper portion of arm 62 the latter is preferably bare.

With arm 62 properly inserted into sleeve 12, pump 26 is activated to produce a negative pressure between −20 mmHg and −85 mmHg inside sleeve 12. Under the influence of negative pressure or suction, flange 20 seals tightly around the upper part of arm 62 to preserve the vacuum inside sleeve 12. At the same time, cooling and circulating system 44 is also activated to cool and pump cooling fluid 30 through cooling blanket 34. In particular, cooling fluid 30 is delivered through supply conduit 42 and recirculated through return conduit 58. Control indicator 46 is used for setting the proper flow rate and temperature of fluid 30.

The device shown in FIG. 1 and described below is merely representative of devices that can be employed to practice the subject invention. Other device configurations are possible, e.g. ones in which the sleeve is replaced with a glove, shoe/boot, etc, and come within the scope of the subject invention.

FIGS. 8 to 13 provide various view of another embodiment of a device that can be employed to practice the subject invention. The features of the system depicted in FIGS. 8 to 13, belonging to AVACore Technologies, Inc. (Palo Alto, Calif.), are preferred for carrying out the methodologies described herein. The system described includes a negative pressure chamber in which to apply or remove thermal energy from a human subject. An improved interface between the chamber and its external environment is provided.

Aquarius, Inc. (Scottsdale, Ariz.) produces a system that may be used or variously modified for use in the stated method(s). However, that system utilizes a "hard" seal interface with a user. The system described herein may utilize a "soft" seal. A "hard" seal is characterized as one designed to altogether avoid air leakage past the boundary it provides. In theory, a "hard" seal will allow a single evacuation of the negative pressure chamber for use in the methods. In practice, however, a "hard" seal can produce a tourniquet effect. Also, any inability to maintain a complete seal will be problematic in a system requiring as much.

A "soft" seal as described herein is characterized as providing an approximate or imperfect seal at a user/seal interface. Such a seal may be more compliant in its interface with a user. Indeed, in response to user movement, such a seal may leak or pass some air at the user/seal interface. In a negative-pressure system designed for use with a soft seal, a regulator or another feedback mechanism/routine will cause a vacuum pump, generator, fan or any such other mechanism capable of drawing a vacuum to respond and evacuate such air as necessary to stabilize the pressure within the chamber, returning it to the desired level. Active control of vacuum pressure in real-time or at predetermined intervals in conjunction with a "soft" seal provides a significant advantage over a "hard" seal system that relies on simply pulling a vacuum with the hopes of maintaining the same.

A further disadvantage over the Aquarius system has more to do with seal configuration than its barrier function. Entry and exit from the Aquarius seal is difficult. Whether "hard" or "soft" in function, the present system provides a two-sided seal configuration. The meaning of this will be more apparent in view of the following figures and descriptive text.

Figure 8:
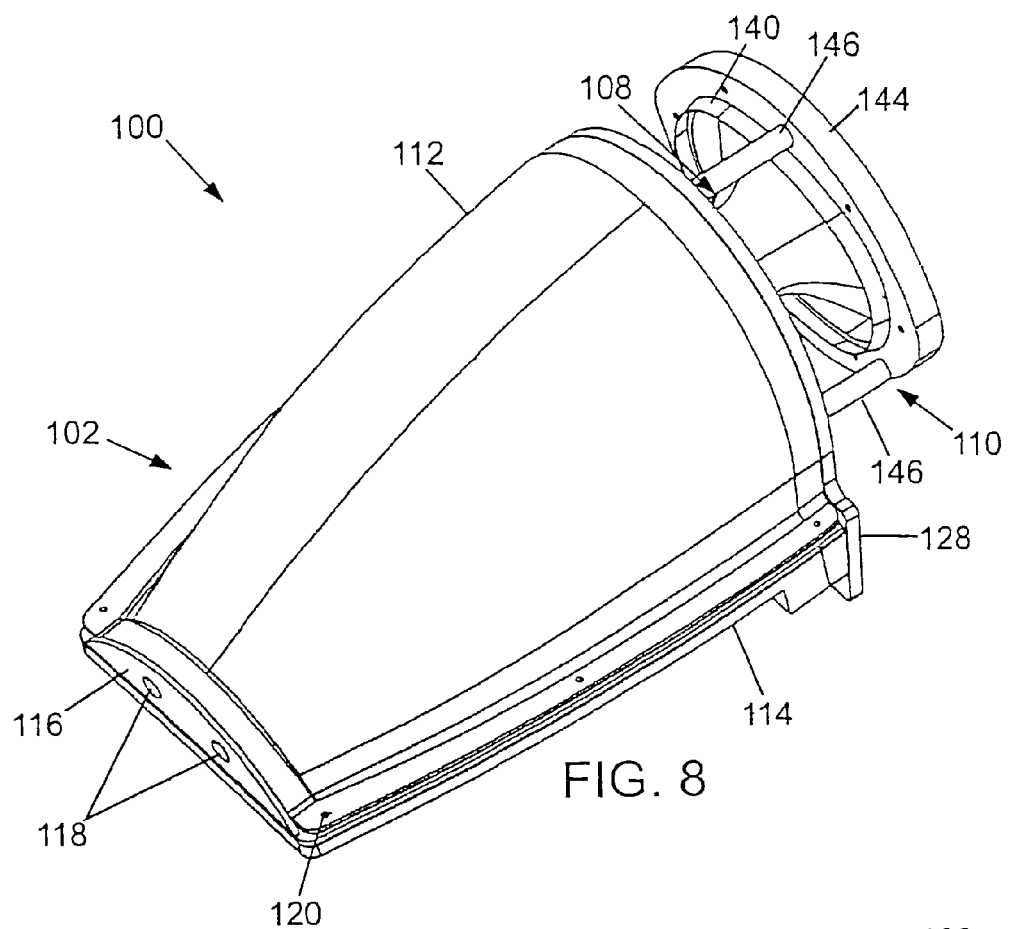
Figure 9:
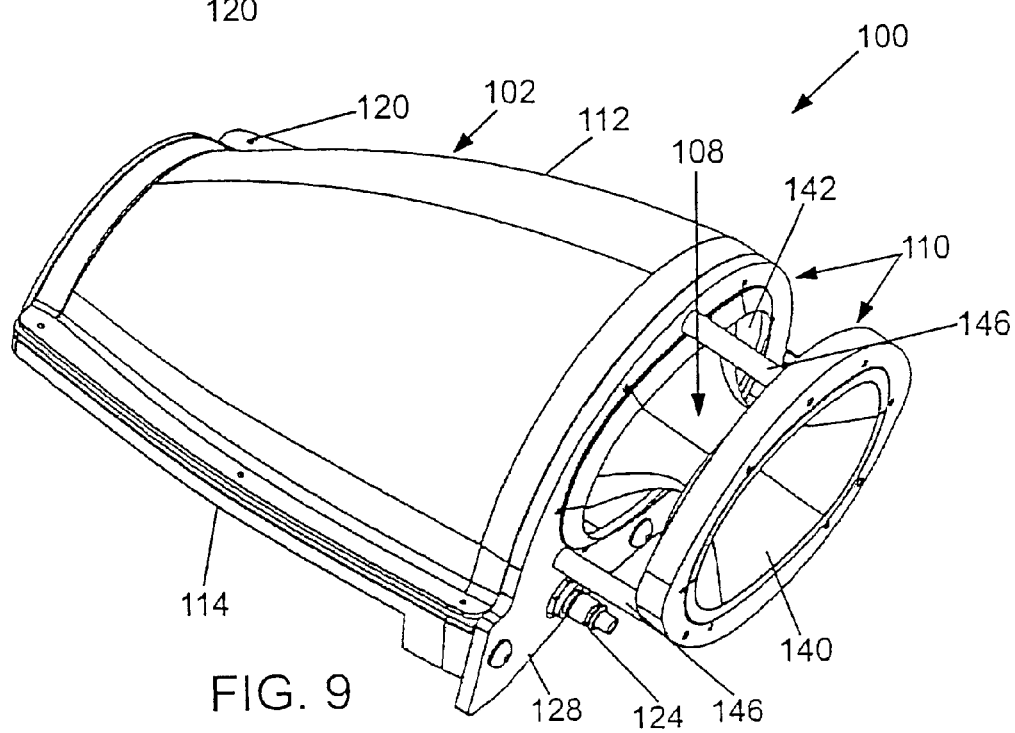
Figure 10:
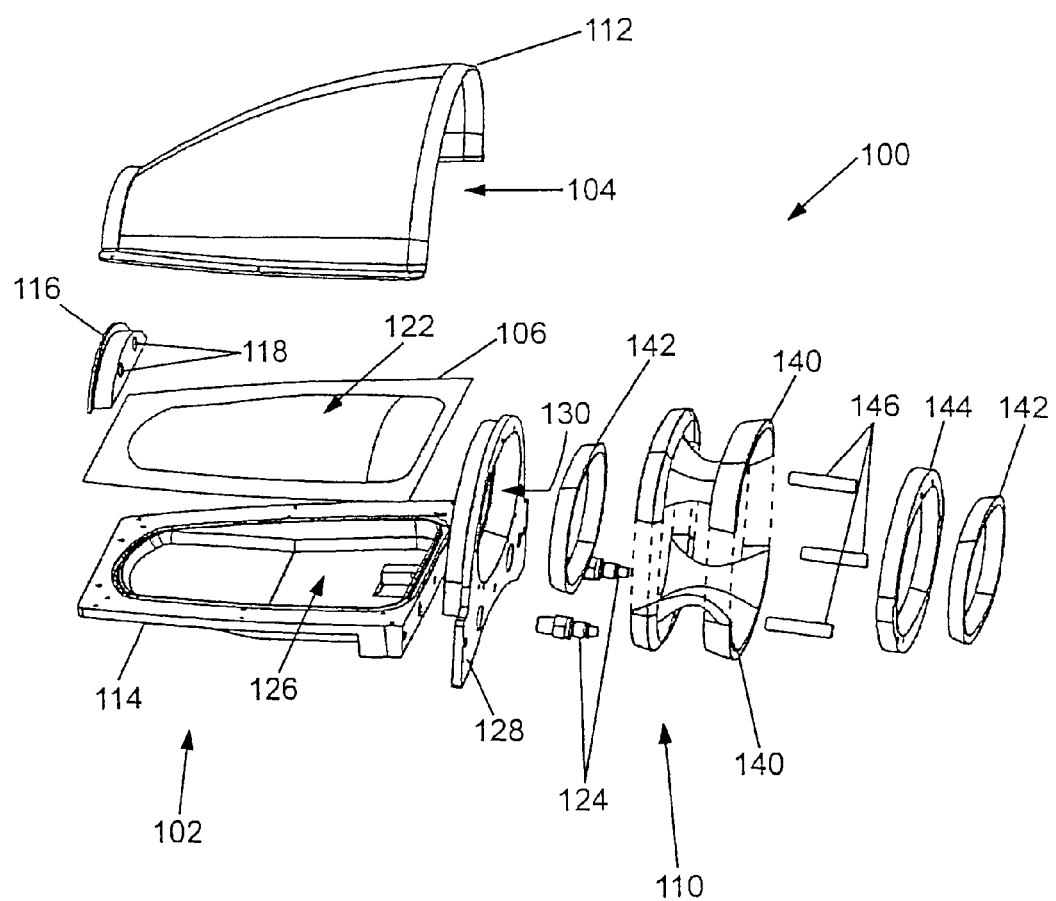

FIGS. 8 and 9 provide fore and aft perspective views of a negative pressure thermal exchange module (100). FIG. 10 provides an exploded view of the same. The system components not shown in the figures include a thermal control or perfusion unit. Such a unit may be adapted to provide a stream of heat exchange media such as water at elevated temperatures, lowered temperatures or both. Further, a vacuum source and regulator optionally used with module (100) are not shown. Any sort of vacuum source or regulator/control mechanism may be used with module (100) as would be apparent to one with skill in the art. Together, these components work to maintain a pressure within module (100) during use between about 20 and 25 inches of $H_2O$ and temperatures for core body cooling between about 19 and 22° C. or temperatures for core body heating between about 40 and 45° C.

As shown, module (100) includes a housing (102) defining a negative pressure chamber (104), a heat-exchange element (106) and a soft, two-sided seal (108) supported by seal frame elements (110).

Housing (102) may be made from a cover (112) and a base (114). Negative pressure chamber (104) is preferably provided between heat exchange element (106) and cover (112). The embodiment shown is adapted to fit the hand of a human user. Chamber (104) is preferably configured to fit a human hand of any size. In order to provide a more space-efficient package, however, it may be more preferably sized to fit 95% of human hand sizes. Alternately, it may be sized for more particularized groups, such as children. It is also contemplated that the housing may be configured to fit a human foot since the under surface of a foot may also be used effectively as a heat exchange surface.

Housing (102) may be constructed from multiple pieces, including an end cap (116) as shown, or it may be provided as a unitary structure. Cap (116) is shown including a ports (118). A first port may be utilized for connection to a vacuum source, while the second may be utilized for a vacuum gauge. Of course, alternate port placement is also possible.

Preferably, housing (102) is made of plastic. Most preferably, the material and design of at least a portion of module (100) are such that housing (102) may be produced by vacuum forming or molding techniques.

Where discrete cover (112) and base (114) portions are used, they may be mechanically secured to one another through bolt holes (120). In such an instance, a gasket or caulking may be employed to seal the periphery of housing (102).

Providing a separable cover (112) and base (114) or heat exchange element (106) provide advantageous access to clean module (100) after use. However, it is contemplated that the top and bottom portions of the module may be fused together, for instance, by ultrasonic welding, chemical bonding or otherwise. Also, as noted above, it is contemplated that housing (102) may be provided in a single piece.

Regardless of the construction, sizing or overall appearance of housing (102), it defines a portion of chamber (104). A heat exchange surface (122) for delivering or accepting a thermal load from a user also defines a portion of chamber (104). A user may directly contact heat exchange surface (122). Alternately, a user may wear a glove or sock or take other prophylactic measures. Heat exchange surface (122) may be provided by a member separate from heat exchange member (106) such as by an intermediate layer of foil, metalized Mylar or another material.

Heat exchange element (106) is preferably made of aluminum or another high thermally-conductive material. It may be in communication with a Peltier device, a desiccant cooling device or an endothermic or exothermic chemical reaction to provide a temperature variance. More preferably, however, heat exchange member (106) is in communication with at an inlet and an outlet (124) to accommodate a flow of perfusion liquid behind heat exchange surface (122). Chilled or heated water may be used to maintain the contact surface of the element at a desired temperature. Optimally, perfusion fluid is run through a series of switchbacks in cavity (126) between element (106) and base (114).

A rear portion of housing (102) and heat exchange member (106) may be provided by plate (128). As depicted, this portion may include provision for inlet and outlet (124) to heat exchange cavity (126) and an opening (130) to chamber (104). A preferred manner of constructing seal (108) is disclosed in connection with plate (128).

Figure 11:
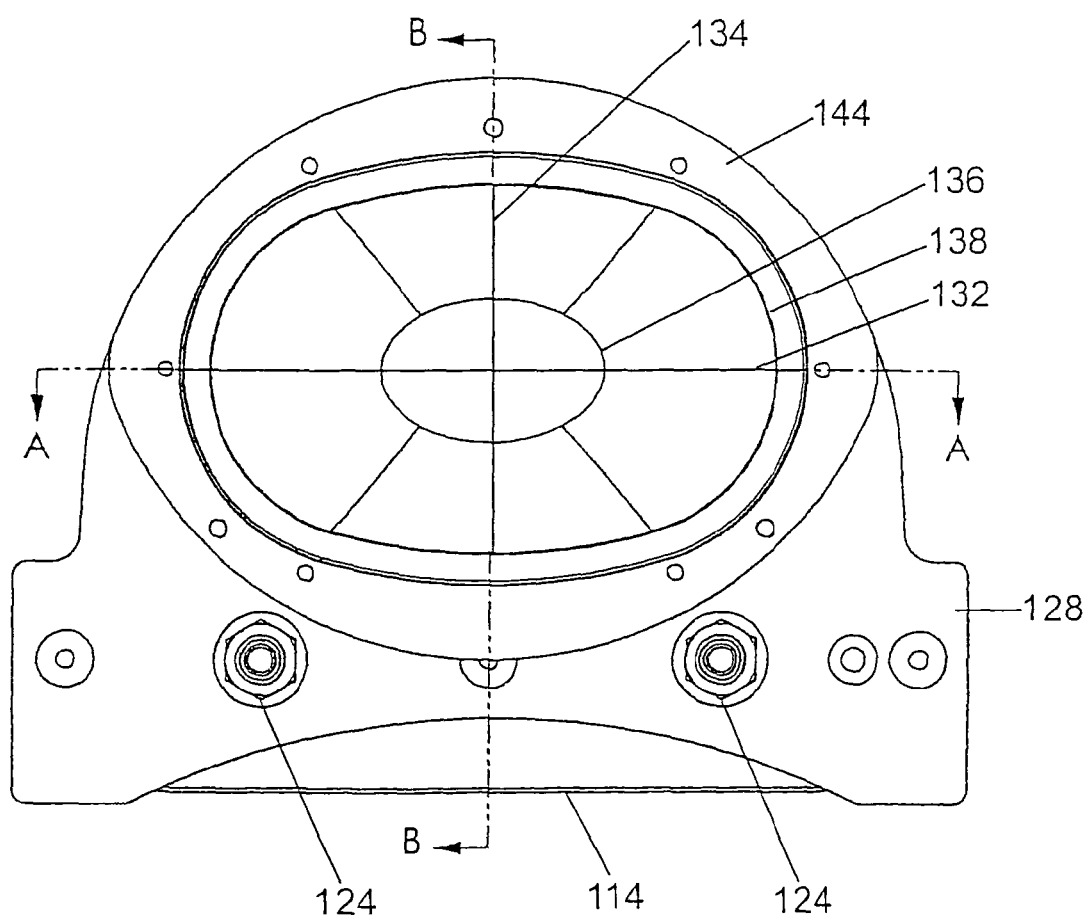

Views detailing preferred geometric aspects of seal (108) are shown in FIGS. 11, 12 and 13. FIG. 11 shows an end-on view of seal (108). Preferably, at least portions of seal (108) are ovalized in form. An elliptical shape may be preferred. A circular shape may also be used. Still, a shape having a major axis (132) and a minor axis (134) will be preferred, at least for the waist opening (136) of seal (108). An ovalized shape approximately corresponds to the shape of the wrist or forearm of a user. A shape having a major axis (132) and a minor axis (134) will also be preferred at chamber opening (130) and seal opening (138). This will assist in providing clearance for hand entry and exit of module (100). It will also simplify the construction of seal webbing (140).

Whether or not ovalized features are utilized for seal (108), it will be shaped roughly like an hourglass. Seal (108) will most closely resemble an hourglass if openings (130), (136) and (138) are circular. When ovalization is applied, different projected views of seal (108)—such as viewed in FIG. 12, for the section taken along line A-A and in FIG. 6 for the section taken along line B-B—display an hourglass shape.

Of course, the shapes depicted may be characterized as other than "hourglass" forms. For instance, profiles of seal (108) may be viewed as hyperbolic or parabolic. Further, simple radiused or semi-circular cross-sections may be utilized in producing seal (108). Further straightened sections may be used, especially, between the openings (130) and (138) and waist (136).

Whatever the case, a two-sided seal with outside openings of a greater size than that of the inside opening is to be used in module (100). This geometry provides for ramps or transition sections for appendage entry and exit. These features assist in stretching the seal interface or waist (136) sufficiently wide to pass a hand or foot both for insertion into and removal from module (100).

Material selection is important in providing such a seal. Clearly, the material must be able to stretch. Further, it should provide a substantial barrier to air flow. To meet each of these criteria, a urethane-backed lycra available from Malden Mills (Malden, Mass.) has proven effective. Still, it is contemplated that other materials may be used. The material (or materials) selected for webbing (140) preferably has a finish that does not grip onto a user so as to complicate entry and exit from module (100). The urethane skin of the referenced material has a satin finish. This decreases friction with the skin and hair of a user.

In addition to providing sufficient stretch, the seal webbing material should also have sufficient strength to avoid being drawn too far into cavity (104) upon the application of vacuum. When in use, the open construction of seal (108) will result in cavity-side webbing material exposed to partial vacuum within chamber (104) to be forced by ambient pressure inward. This self-inflation phenomena observed for the chamber-side of the seal may be of assistance in providing seal patency with a user. However, if too much material bows inward, it will result in an uncomfortable or disconcerting displacement of the user's hand or foot into the device. Accordingly, with proper material choice, the side of seal (108) opposite chamber (104) provides not only a transition section for entry and exit, but also a stabilizing feature for seal position.

Seal (108) is preferably formed by a sleeve made by stitching two pieces of webbing material (140) together where they are shown broken apart in the exploded view of FIG. 10. By constructing the sleeve from two or more pieces, complex shapes can be easily produced. To secure the sleeve webbing (140) in place to form seal (108), it is folded over rings (142) at each end as variously depicted. Then the cavity-side ring and webbing is captured in opening (130) of plate (128). The opposite side of seal webbing (140) is captured between outer ring (142) and retainer member (144). Standoffs (146) or equivalent structure space plate (128) and ring retainer (144) apart to define the overall length of seal (108). Of course, the length of the standoffs or seal may be varied as well as the other parameters of seal (108) that effect fit.

In this respect, it is noted that it may be desirable to provide a longer overall seal in some instances. Increasing overall length provides further design flexibility with seal shape. This may be best taken advantage of by increasing the length of waist (136) to provide greater seal surface contact with a user. This may beneficially reduce any undesirable constricting effects. Furthermore, it is to be appreciated that the nature of the material used for the seal webbing (140) may be advantageously varied. While the noted lycra-based material is isotropic in nature, an anisotropic material or effect may be preferred for the webbing. This is to say that greater radial expansion of the sleeve may be desirable, whereas longitudinal compliance may not be. By reducing compliance along the axis of the sleeve relative to a radial component, it will tend to be drawn into chamber (104) to a lesser degree upon the application of vacuum. For a very high-stretch material, this will allow for smaller seal openings to fit the same population (since they can still stretch webbing (140) radially and have it return sufficiently to form a desired seal), without forfeiting the full set of advantages that the two-sided seal described offers.

Such an anisotropic effect may be achieved in a number of ways. It may be accomplished by providing longitudinal reinforcement member(s) associated with the webbing. They may be incorporated through braiding techniques, by bonding/affixing stiffener(s) to the sleeve surface or by other means as would be apparent to one with skill in the art.

Regardless of the particulars of seal construction and whether it is utilized to provide a "hard" or "soft" user interface, the dual-sided seal disclosed provides a superior manner of carrying out the methodology noted above. Though a "soft" two-sided seal as shown in the figures is preferred for its elegance in approach and proven effectiveness, a "hard" or more complex "soft" seal approach might sometimes be desired.

In order to utilize the dual-sided seal in a "hard" approach, supplemental forcing means may be provided to apply pressure around seal waist (136). Mechanical means such as at least one of a strap, belt or cinch may be used. Alternately an inflatable cuff or bladder portions around the periphery of the seal may be employed. While the system complexity will increase due to provision for providing the supplemental pressure and controlling it by either automated or manual means, certain potential advantages arise.

It may enable a single-evacuation procedure for chamber (104) rather than relying on constant or periodic vacuum replenishment. It may also provide greater design flexibility for seal (108). Particularly, by providing another variable to utilize in design decisions, a lesser emphasis may be placed on webbing material choice or opening sizing since the supplemental forcing capacity may be used to shape the seal as desired in use. Further, it may enable fitting seal (108) to a wider range of a populous for a given configuration of hard elements, such as those that make-up seal frame (110).

Supplemental forcing or seal shaping means may also be used to produce a more complex "soft" seal than that described above. As with a "hard" seal approach, this would open design and fit possibilities. Forcing or seal shaping parameters may, again, be controlled manually or automatically. Except, in a complex "soft" seal, the control of pressure applied to waist (136) is gauged to provide a compliant feel or fit. Since the application of pressure on the seal interface with the user may be the only difference between a complex "soft" seal approach and a "hard" seal approach utilizing the dual-sided configuration, the same apparatus may be configured to function in either manner, for instance, by providing variable pressure control.

The following examples are offered by way of illustration and not by way of limitation.

Experimental

I. Pull Up Test

A. Introduction

Pull-ups were used as exercise regime to increase metabolic heat production and produce hyperthermia.

Subject is a 33 year old male who maintained a regular regime of strength conditioning prior to this study.

Trials were run 2 to 3 times per week

Each trial consisted of sets pull-ups performed to exhaustion at 3.5 minute intervals. Tympanic membrane temperature was recorded continuously B. Methods Core cooling is achieved by placing hand and forearm under negative pressure and cooling skin with water perfused pad.

Subject places hand and forearm in sealed chamber shown in FIG. 1.

Air is withdrawn from chamber to create subatmospheric pressure.

Cool water (17 to 20° C.) is pumped through pad surrounding hand and forearm

Process takes two to three minutes and can extract excess heat produced by large dynamic muscle exercise.

Figure 7:
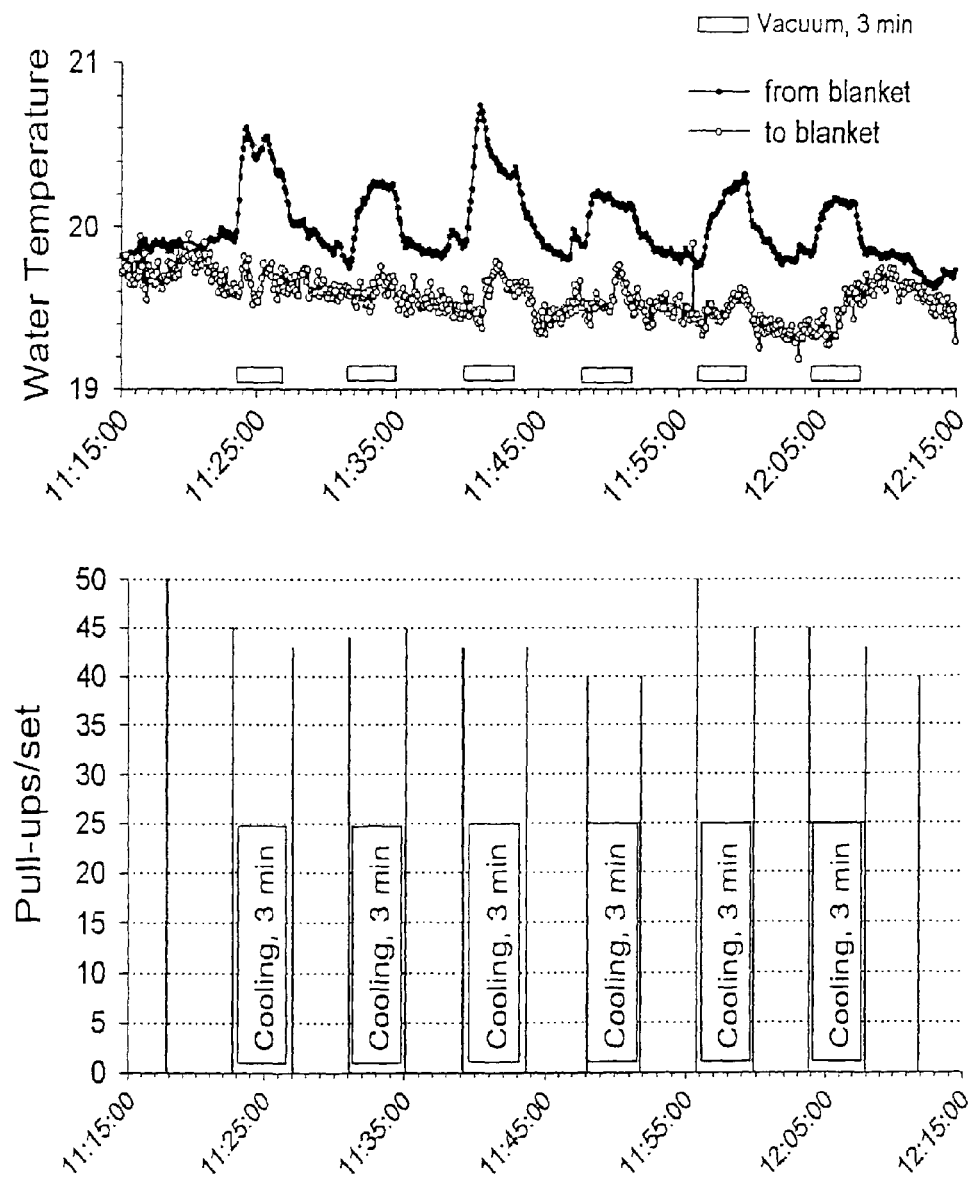
FIG. 7 provides a graphical representation of the results from an assay demonstrating that heat can be extracted from the core body of a subject using the device shown in FIG. 1.

Heat extraction is calculated from water perfusion rate and the difference between inlet and outlet temperatures. See FIG. 7.

Sweating is reduced.

C. Core Cooling can Partially Reverse Muscle Fatigue of Large Dynamic Muscles Exercised to Exhaustion.

Subject completes as many pull-ups as possible in individual sets spaced 3.5 minutes apart.

Capacity for power output declines with repeated sets of pull-ups.

One three minute core cooling returns power output to initial value.

Figure 2:
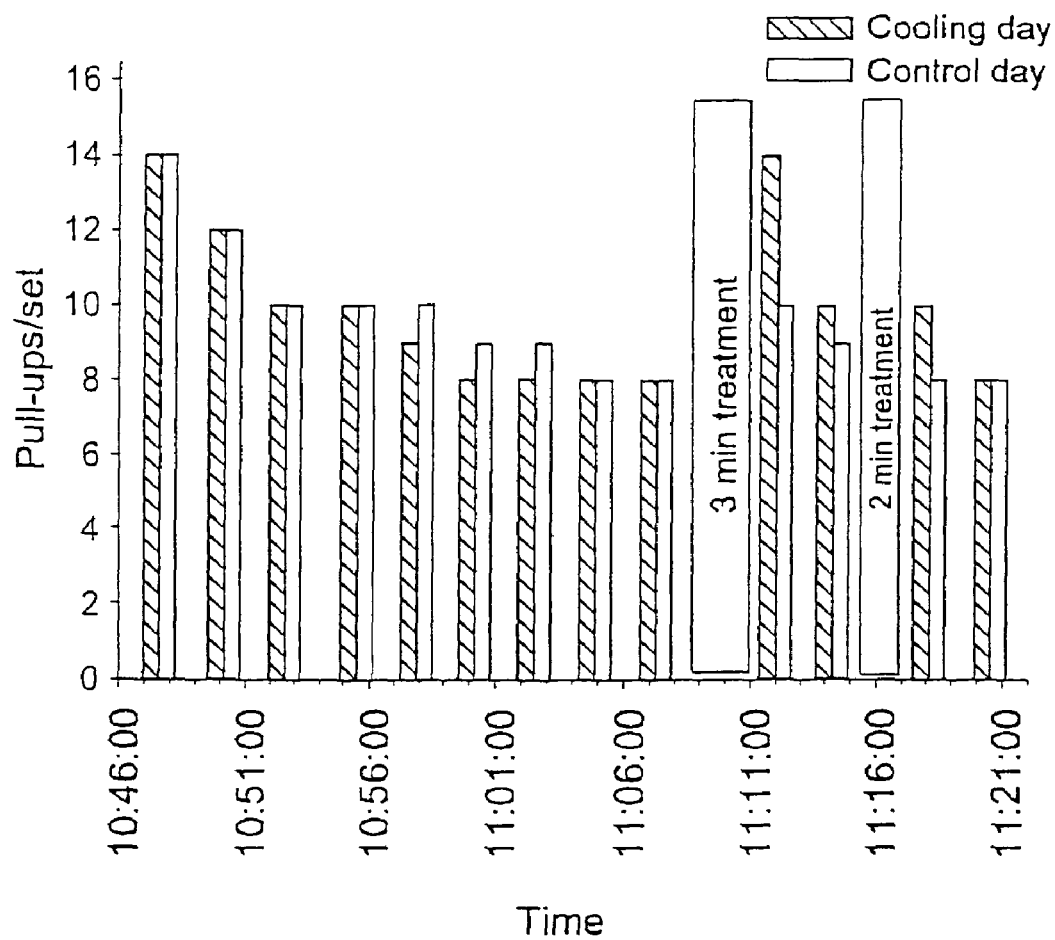
FIG. 2 provides a graphical representation of the results from an assay demonstrating that core cooling can partially reverse muscle fatigue of large dynamic muscles exercised to exhaustion.

A subsequent two-minute core cooling also increases subsequent power output. The results are graphically illustrated in FIG. 2.

D. Core Cooling Restores Power Output of Fatigued Large Dynamic Muscles.

Subject was asked to do pull-ups to exhaustion every 3.5 minutes for 45 minutes.

First set of pull-ups averaged 14

Ninth set of pull-ups averaged 8

Following 3 minutes of core cooling the tenth set of pull-ups averaged 13.

In control runs the tenth set of pull-ups averaged 10.

Figure 3:
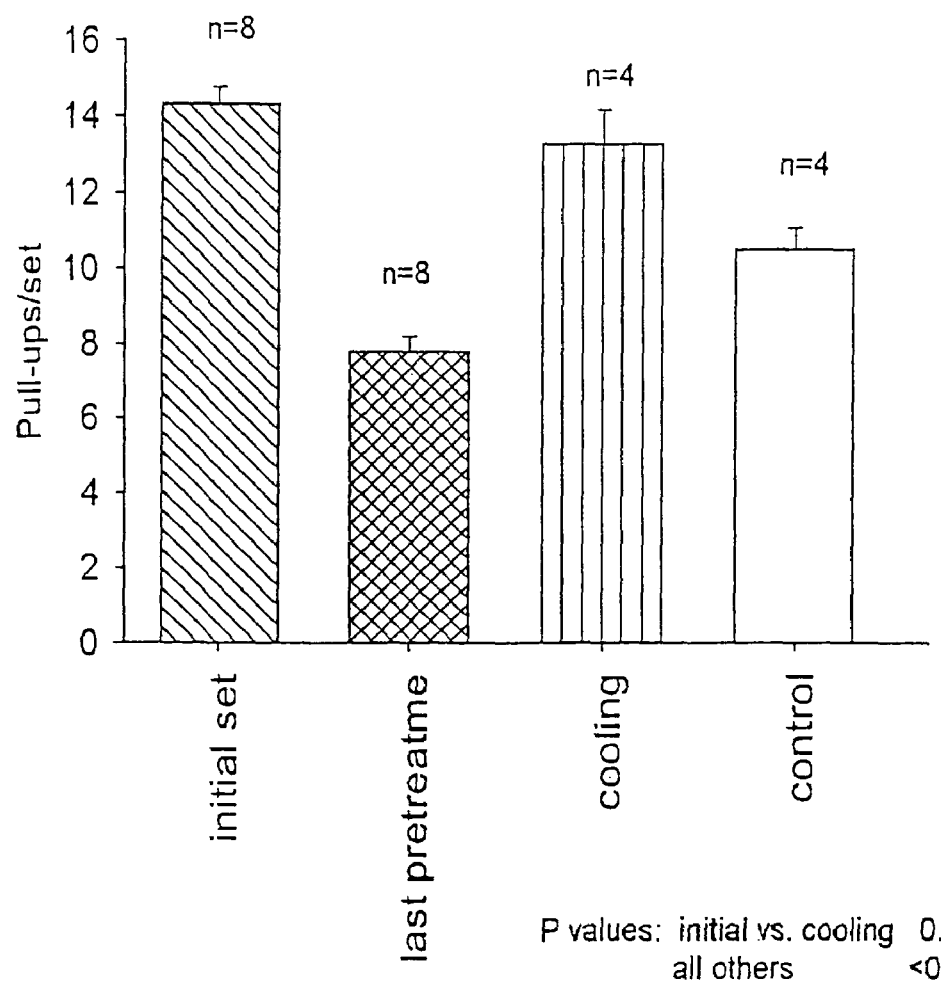
FIG. 3 provides a graphical representation of the results from an assay demonstrating that core cooling restores power output of fatigued large dynamic muscles.

Thus, power output following core cooling was increased 60% over pretreatment and 33% over control The results are graphically illustrated in FIG. 3.

E. Regular Exercise to Exhaustion Results in Slow Increase in Strength (Conditioning)

Subject did pull-ups to exhaustion in sets spaced 3.5 minutes apart for 45 minutes about twice weekly Over 6 weeks the capacity of the subject for pull-ups increased by less than 2 fold.

Figure 4:
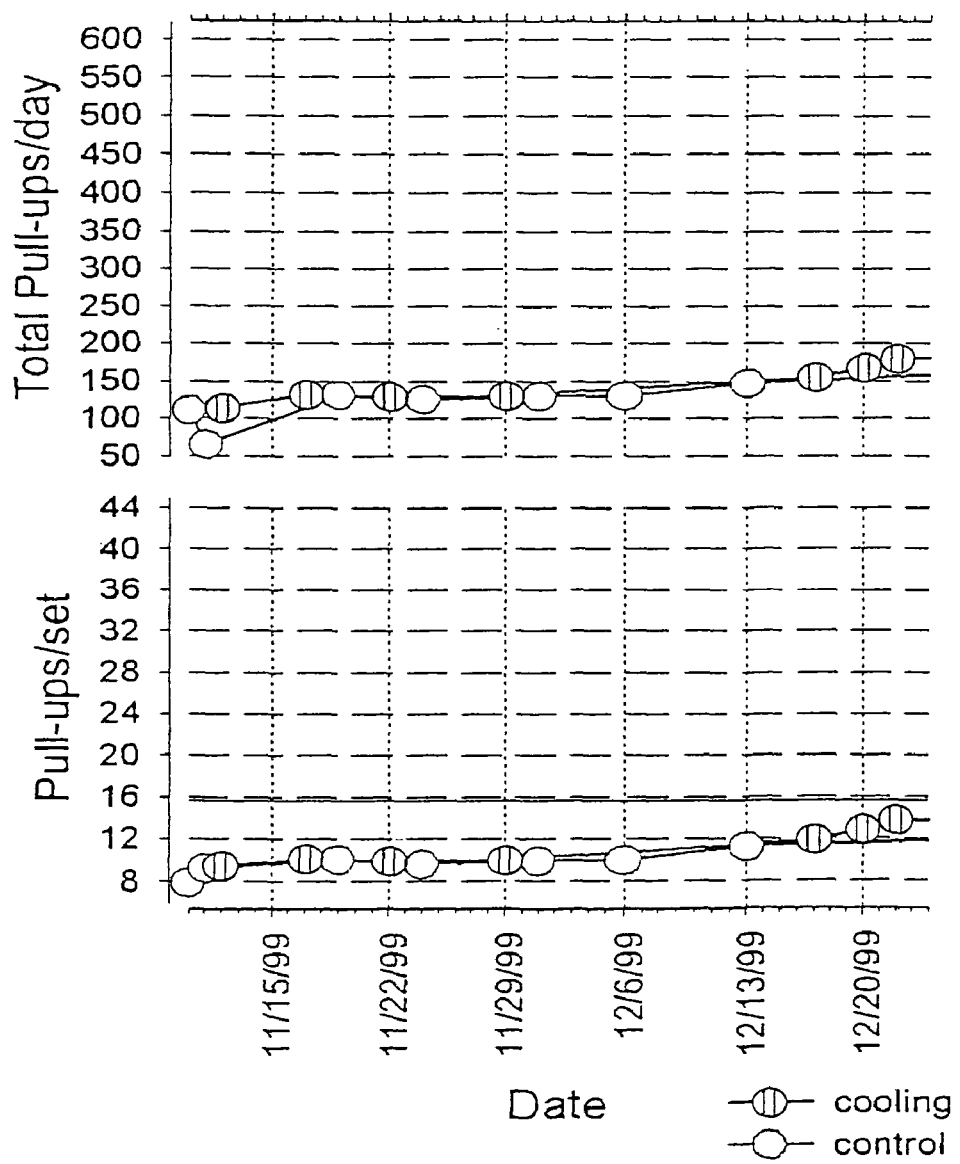
FIG. 4 provides a graphical representation of the results from an assay demonstrating that regular exercise to exhaustion results in slow increase in strength (conditioning).

The results are graphically illustrated in FIG. 4.

F. Repeated Core Cooling Increases Subject's Capacity During Individual Conditioning Episodes.

Subject was requested to do pull-ups to exhaustion at 3.5 minute intervals.

Without core cooling the subject's capacity steadily declined from an initial 20 to a final 9 pull-ups.

With core cooling pull-up capacity exceeded control sets at all times following initial set, and plateaued at 14 pull-ups for most of the trial.

Thus, the challenge of this workout routine was 17% greater with core cooling.

Figure 5:
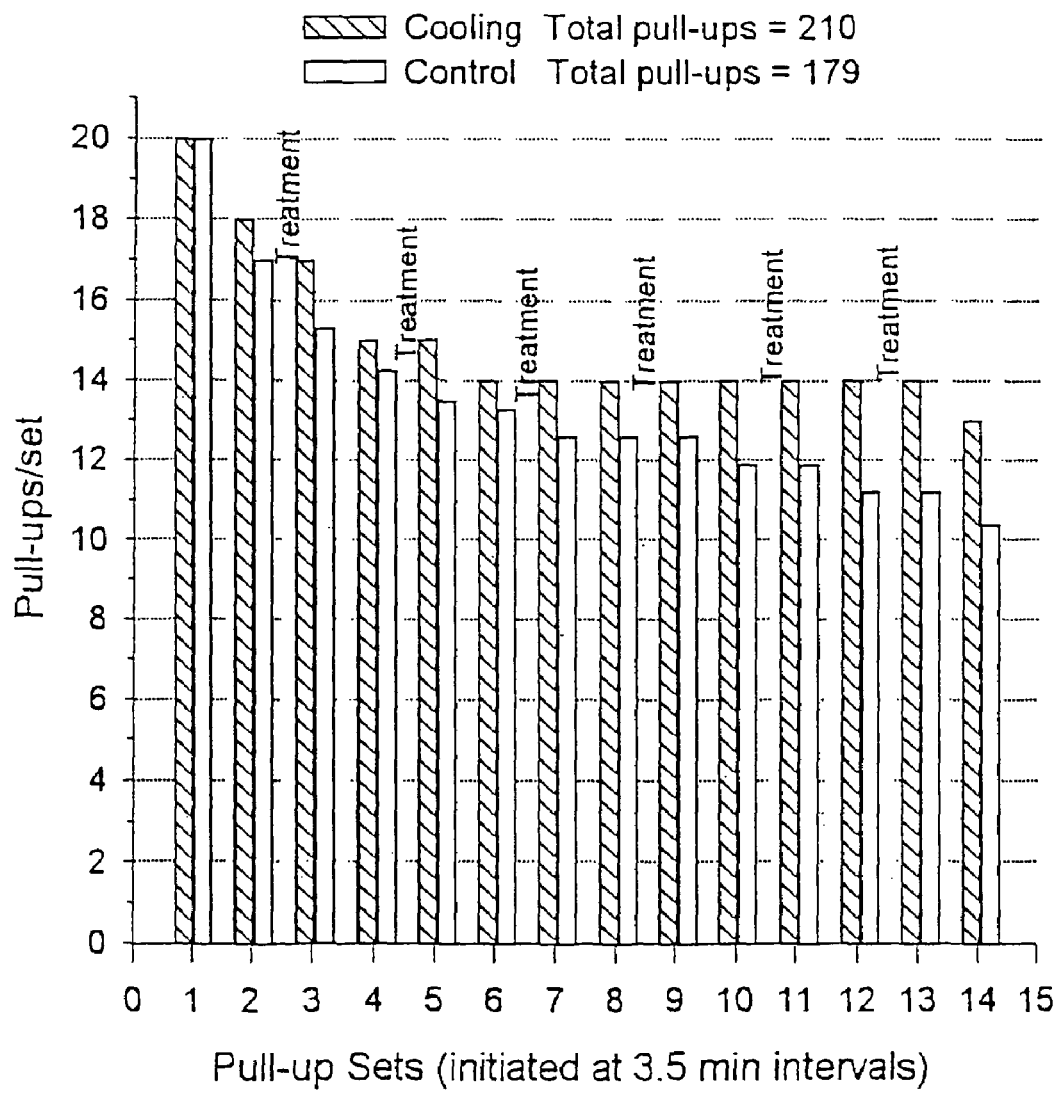
FIG. 5 provides a graphical representation of the results from an assay demonstrating that repeated core cooling increases a subject's capacity during individual conditioning episodes.

The results are graphically illustrated in FIG. 5.

G. Core Cooling During Conditioning Enhances Strength Increases.

During prior 6 weeks subject did routine 2 to 3 times per week with one or two core coolings on experimental days. Over that time he almost doubled his capacity from about 100 to less than 200.

During the 6 weeks shown in this figure, the subject did conditioning routine 2 to 3 times per week with repeated core cooling in every other trial. His capacity increased more than 3 fold, from less than 200 to more than 600.

Gains were seen only during cooling days, but increases in strength carried over to control days.

Figure 6:
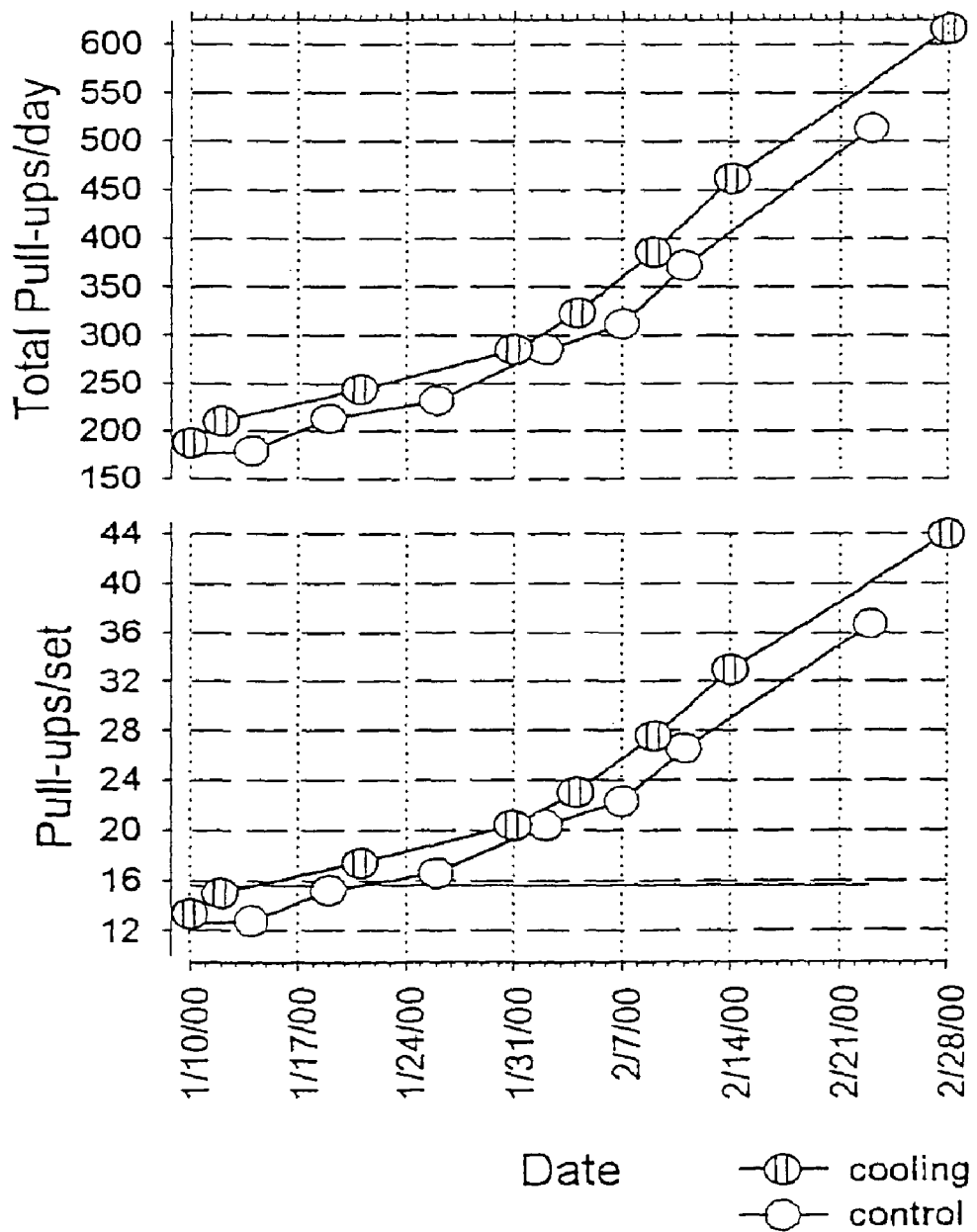
FIG. 6 provides a graphical representation of the results from an assay demonstrating that core cooling during conditioning enhances strength increases.

The results are graphically illustrated in FIG. 6.

II. Additional Pull-Up Experiment

A. Basic procedure:

14 sets of pull-ups with a 3.5 min. rest period between sets. Workouts were 2-3 days/week for 5 control weeks and 5 weeks with cooling.

B. Results.

Complete results from 5 subjects have been obtained. The results confirm the initial observation seen in Example I above. In 4 out of 5 subjects repeated cooling between sets of aerobic exercise increased the workout capacity. It is likely that in the non-responsive subject the cooling load applied to the heat exchange surfaces induced a local vasoconstriction that blocked the transfer of the thermal load to the body core.

Example III. Cooling During Circuit Weight Training.

A. Procedure:

Subjects: 20 members of the Stanford University varsity football team, 12 experimental subjects, 8 controls. Basic procedure: NCAA rules govern the timing and duration of strength and conditioning programs for intercollegate athletes. Therefore these training sessions are carefully regimented and monitored to maximize the benefits of the training during these sanctioned training sessions. For each day of training the individual athletes are assigned a personalized workout routine that specifies the sequence of exercises to be performed, the target performance at each exercise station, and the rest interval between the exercise stations. During the summer and winter strength and conditioning programs the experimental subjects were cooled during the rest intervals between exercise stations. In these studies, the duration of exposure to the cooling device was either 45 seconds or 1.5 min. The percent of times the subjects achieved their daily performance targets served as an index for assessing relative changes in fitness levels. Efficacy of the treatment was determined by differences between control and experimental conditions in the % of times that the subjects achieved their targeted performance levels.

B. Results:

Under control conditions, subjects reached their target performance goals 30-50% of the time. Eight of 12 experimental subjects achieved their target performance goals 70-80% of the time. Performance by the remaining 4 experimental subjects was indistinguishable from the control group. Factors that could have effected whether an individual responded to treatment include; the temperature at the skin surface (if too cold a local vasoconstrictive response will be elicited) and the duration of treatment (45 sec treatments may be insufficient to appreciably effect the thermal condition of the body core of certain subjects).

Example IV. Temperature Manipulations During Exercise in a Hot Environment (33-34 Degrees C., 27-90% Relative Humidity):

A. Procedure:

In this study, anaerobic exercise in a hot environment is used as a means of increasing internal boy temperature. Esophageal and tympanic membrane temperatures and heart rate are continuously measured. Water loss is determined by weight loss during exercise. Basic protocol; ride a stationary bicycle at a fixed load for 60 min or to exhaustion. Manipulations: control (no cooling), cooling during exercise, or cooling during recovery from exercise.

B. Results:

Four individuals were studied. Cooling during exercise reduces water loss (20-30%), peak heart rate (10-15%), and rate of core temperature rise (25-35%). The bottom line result is that cooling in an extreme hot environment allows an individual to sustain a given work load for a longer period of time. Cooling subsequent to exercise speeds recovery as determined by rate of heart rate and core temperature declines.

It is evident from the above results and discussion that the subject invention provides a convenient method for extracting thermal energy or heat from the core body of a subject. Benefits of the subject invention include the non-invasive, simple to perform nature of the subject methods which provide for better patient compliance. Additional benefits include the non-pharmacological basis of the methods.

It is also evident from the above results and discussion that the subject invention provides a convenient method for significantly improving the ability of a mammal to perform a physical task. Benefits of this embodiment of the subject invention include the non-invasive, simple to perform nature of the subject methods. Additional benefits include the non-pharmacological basis of the methods. In view of the above discussion and results, it is readily apparent that the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for extracting thermal energy from the core body of a mammal, said method comprising:
    (a) enclosing a portion of said mammal in a sealed enclosure having a two-sided seal configuration to produce an enclosed portion of said mammal;
    (b) contacting a surface of said enclosed portion with a low temperature medium under negative pressure conditions for a period of time sufficient to extract thermal energy from the core body of said mammal, wherein said low temperature medium has a temperature below said mammal's normal physiologic temperature but above a temperature that results in localized vasoconstriction at said surface.

2. The method according to claim 1, wherein said portion of said mammal is a limb or a portion thereof.

3. The method according to claim 2, wherein said limb is selected from the group consisting of an arm and a leg.

4. The method according to claim 3, wherein said portion is a heat exchange surface.

5. The method according to claim 4, wherein said heat exchange surface is selected from the group consisting of a sole and a palm.

6. The method according to claim 2, wherein said sealed enclosure under said negative pressure conditions has a pressure ranging from about −20 to about −80 mm Hg.

7. The method according to claim 2, wherein said low temperature medium has a temperature ranging from about 15 to about 35° C.

8. The method according to claim 2, wherein said period of time ranges from about 0.5 min to about 24 hrs.

9. The method according to claim 1, wherein said mammal is a human.

10. A method for enhancing the ability of a mammal to perform a physical procedure, said method comprising:
    (a) enclosing a portion of said mammal in a sealed enclosure having a two-sided seal configuration to produce an enclosed portion of said mammal;
    (b) contacting a surface of said enclosed portion with a low temperature medium under negative pressure conditions at least once during said physical procedure for a period of time sufficient to enhance the ability of said mammal to perform said physical procedure, wherein said low temperature medium has a temperature below said mammal's normal physiologic temperature but above a temperature that results in localized vasoconstriction at said surface.

11. A device for extracting thermal energy from the core body of a mammal, said device comprising:
    (a) a sealable enclosure having a two-sided seal configuration dimensions sufficient to produce an enclosed portion of a mammal;
    (b) a negative pressure producing element that produces negative pressure conditions in said sealable enclosure; and
    (c) a cooling element for producing a reduced temperature medium in said sealable enclosure;
    (d) wherein said devices is adapted to avoid localized vasoconstriction on the surface of an enclosed portion of a mammal.

* * * * *